United States Patent [19]
Carles et al.

[11] Patent Number: 6,037,140
[45] Date of Patent: Mar. 14, 2000

[54] SELECTIVE MEDIA FOR THE CULTURE AND ISOLATION OF GRAM BACTERIA, ANTIBIOTIC COMPOSITION

[75] Inventors: Benoit Carles, Armentieres; Jean-Pierre Facon, Lille, both of France

[73] Assignee: Pasteur Sanofi Diagnostics, Marnes la Coquette, France

[21] Appl. No.: 08/729,604

[22] Filed: Oct. 11, 1996

[30] Foreign Application Priority Data

Oct. 13, 1995 [FR] France ..................... 95 12048

[51] Int. Cl.[7] ............................................ C12Q 1/24
[52] U.S. Cl. ...................... 435/30; 514/18; 514/37; 514/38; 514/39
[58] Field of Search ................. 514/18, 37, 38, 514/39; 435/30

[56] References Cited

U.S. PATENT DOCUMENTS

| | | | |
|---|---|---|---|
| 4,340,671 | 7/1982 | Gibson | 435/32 |
| 5,446,070 | 8/1995 | Montelle | 514/772.6 |
| 5,635,484 | 6/1997 | Ayrev et al. | 514/18 |

FOREIGN PATENT DOCUMENTS 0 243 015  10/1987  European Pat. Off. .

OTHER PUBLICATIONS

Y. C. Faur, et al., "A New Medium For The Isolation Of Pathogenic Neisseria (NYC Medium) I. Formulation And Comparisons With Standard Media," *Health Laboratory Science*, vol. 10, No. 2, Apr. 1973, pp. 44–54, XP000573744.

Y. C. Faur, et al., "A New Medium For The Isolation Of Pathogenic Neisseria (NYC Medium) II. Effect Of Amphotericin B And Trimethoprim Lactate On Selectivity," *Health Laboratory Science*, vol. 10, No. 2, Apr. 1973, pp. 55–60, XP000574294.

Y. C. Faur, et al., "The Selectivity Of Vancomycin And Lincomycin In NYC Medium For The Recovery Of *N. Gonorrhoeae* From Clinical Specimens", *Health Laboratory Science*, vol. 15, No. 1, Jan. 1978, pp. 22–26, XP000573746.

I. Phillips, et al., "Diagnosis Of Gonorrhoea By Culture On A Selective Medium Containing Vancomycin, Colistin, Nystatin And Trimethoprim (VCNT)," *Brit. J. Vener. Dis.*, vol. 48, Aug. 1972, pp. 287–292, XP000574390.

Database WPI, Section Ch, Week 8546, Derwent Publications Ltd., London, GB; Class D05, AN 85–287886, XP002006573 & JP–A–60 199 398 (Eiken Kagaku KK), Oct. 8, 1985.

*Primary Examiner*—Elli Peselev
*Attorney, Agent, or Firm*—Jacobson, Price, Holman & Stern, PLLC

[57] ABSTRACT

This invention relates to a selective medium for the culture and isolation of Gram$^-$ bacteria comprising at least one antibiotic specifically active against Gram$^+$ bacteria and at least one bacteriocin.

33 Claims, No Drawings

SELECTIVE MEDIA FOR THE CULTURE AND ISOLATION OF GRAM BACTERIA, ANTIBIOTIC COMPOSITION

The present invention relates, on the one hand, to selective media for the culture and isolation of Gram-negative (Gram$^-$) bacteria and, on the other hand, to antibiotic compositions useful for the culture and isolation of these same microbes.

The european Patent published under the number EP-A-243 015 which claims a culture medium for the selective isolation of the pathogenic Neisseria bacteria is known in the prior art, the said medium comprising an antibiotic composition including a mixture of vancomycin and lincomycin. The combination of these two antibiotics, having an inhibitory activity towards Gram$^+$ bacteria, is used, with other inhibitory agents, to selectively isolate pathogenic Neisseria bacteria.

Moreover, nisin is known to be a bacteriocin, that is to say an antibiotic of the polypeptide type produced by some strains of *Lactococcus lactis* or *Streptococcus lactis*. This antibiotic exhibits a broad spectrum towards Gram$^+$ microorganisms, including spore-forming microorganisms. The publication by Stevens et al. (Nisin Treatment for inactivation of Salmonella Species and Other Gram-negative Bacteria, A.E.M. (1991), December, pp. 3613–3615) which describes the activity of nisin is also known. Thus, in addition to its inhibitory activity known against Gram$^+$ bacteria and used in the food sector for the preservation of sensitive foodstuffs such as dairy products (Delves-Broughtonj., Nisin and its uses as a food preservative, Food Technol., (1990) 4, pp. 100–112) or for the purpose of controlling a fermentation process such as the production of lactic acid in wine (Hanlin M. B. et al., Bacteriocins of lactic acid bacteria in combination have greater antibacterial activity, Journal of Food Protection, (1993), 56: pp. 252–255), nisin is described in combination with a chelating agent as having an inhibitory activity towards numerous species of Salmonella and also towards other enterobacteria, these microorganisms all being aerobic Gram$^-$ bacteria (facultative anaerobes).

The problem of persons skilled in the art, when they develop selective media for the culture and isolation of bacteria, is to find a compromise between specificity and sensitivity, sensitivity being defined as the capacity to detect positive samples, and specificity as the ability of the test not to generate false positives.

The present invention provides a solution to this problem for the development of specific culture media for the growth and isolation of Gram$^-$ bacteria. Indeed, the Applicant has developed selective culture media, the said media comprising the combination of one or more bacteriocins active against Gram$^+$ bacteria and one or more antibiotics specifically active against Gram$^+$ bacteria. This combination makes it possible to increase the selectivity of the media by enhancing efficacy and by broadening the spectrum for inhibition of Gram$^+$ bacteria, while preserving a very good sensitivity of the media towards the microorganism to be isolated.

The present invention therefore relates to selective media for the culture and isolation of Gram$^-$ bacteria, the said media comprising the combination of one or more antibiotics specifically active against Gram$^+$ bacteria and one or more bacteriocins. The culture media of the invention may be liquid or agar culture media.

A preferred variant of the selective medium according to the invention is a medium comprising vancomycin and/or teicoplanin as antibiotic specifically active against Gram$^+$ bacteria and nisin as bacteriocin. The media according to the invention may, in addition, contain antifungal agents.

Advantageously, the selective medium according to the invention is a medium for the culture and isolation of Gram$^-$ anaerobic bacteria characterized in that it comprises, in addition, an antibiotic specifically active against Gram$^-$ aerobic bacteria.

According to another advantageous variant, the invention also relates to a medium specific for the growth and isolation of parasitic Gram$^-$ aerobic bacteria such as the pathogenic Neisseria bacteria.

The subject of the invention is therefore also a selective culture medium for the growth and isolation of the pathogenic Neisseria bacteria comprising at least one antibiotic specifically active against Gram$^+$ bacteria and at least one bacteriocin, characterized in that it comprises, in addition, a mixture composed of antibiotics active against Gram$^-$ bacteria other than Neisseria and/or antibiotics active against Proteus and/or agents active against yeasts. Preferably, this medium comprises a mixture composed of colymycin, trimethoprim and amphotericin B.

In the present invention, it is understood by:

"bacteriocin", toxins produced by certain bacterial strains, such as for example nisin, pediocin A, lacticin;

"antibiotics specifically active against Gram$^+$ bacteria", antibiotics such as vancomycin, teicoplanin and those of the MLS family (Macrolides, Lincosamides and Streptogramines);

"antibiotics specifically active against Gram$^-$ aerobic bacteria", antibiotics such as for example nalidixic acid, aminosides (kanamycin and the like);

"antifungal agent", compounds active against yeasts such as for example amphotericin B, nystatin;

"nutrient base", a medium containing especially peptones, a yeast extract, salts;

"enrichment supplement", a medium containing especially vitamins, amino acids and/or glucose;

"selective supplement", a mixture of one or more antibiotics and/or agents active against certain microorganisms which it is desired to eliminate.

A concentration of antibiotic(s) specifically active against Gram$^+$ bacteria, such as vancomycin and/or teicoplanin or MLS, of between 1 and 10 mg/l, and still more preferably a concentration of 2.5 mg/l is preferably used in the selective media according to the invention.

The quantities of bacteriocins used are between 10 and 100 mg/l, and preferably from 50 to 60 mg/l.

The antibiotic specifically active against Gram$^-$ aerobic bacteria is used at a concentration of between 5 and 50 mg/l, and preferably 10 mg/l.

The present invention also relates to bactericidal compositions for the culture and specific isolation of Gram$^-$ bacteria comprising at least one antibiotic specifically active against Gram$^+$ bacteria chosen from vancomycin, teicoplanin or a mixture of both, or antibiotics of the MLS group, and at least one bacteriocin.

Preferably, these compositions are intended for the culture and specific isolation of Gram$^-$ anaerobic bacteria, characterized in that they comprise, in addition, an antibiotic specifically active against Gram$^-$ aerobic bacteria, chosen from nalidixic acid or aminosides, such as kanamycin.

According to another advantageous embodiment, the said compositions are compositions for the isolation and culture of pathogenic Neisseria comprising at least one antibiotic specifically active against Gram$^+$ bacteria and at least one bacteriocin, characterized in that they comprise, in addition, colymycin, trimethoprim and amphotericin B.

The invention finally relates to the uses of the said compositions for the manufacture of selective media for the culture and isolation of Gram− bacteria, more particularly of anaerobic Gram− bacteria or of pathogenic Neisseria.

The following examples make it possible to illustrate the invention.

EXAMPLE 1

Selective medium for the growth and isolation of Gram− anaerobic bacteria.

Tests were carried out to compare the medium which is the subject of the present invention with a conventional medium or a medium comprising a bacteriocin as sole agent inhibiting the growth of Gram+ bacteria.

The first medium, designated hereinafter "medium A", contains all the elements of the nutrient base, an enrichment supplement, vancomycin and nalidixic acid.

The second medium, designated "medium B", contains all the elements of the nutrient base, an enrichment supplement, nalidixic acid and nisin.

The third medium, designated "medium C", corresponds to the medium according to the invention and contains all the elements present in medium A and medium B.

The concentrations indicated are the final concentrations for one liter of preparation.

TABLE I

| PRODUCT | MEDIUM A | MEDIUM B | MEDIUM C |
|---|---|---|---|
| Nutrient base for anaerobes | 3% | 3% | 3% |
| Enrichment supplement | 8 mg/l | 8 mg/l | 8 mg/l |
| Nalidixic acid | 10 mg/l | 10 mg/l | 10 mg/l |
| Vancomycin | 2.5 mg/l | 0 | 2.5 mg/l |
| Nisin | 0 | 60 mg/l | 60 mg/l |
| Agar | 13 g/l | 13 g/l | 13 g/l |
| Defibrinated blood | 5% | 5% | 5% |

The base for anaerobes comprises compounds promoting the growth of Gram− anaerobic bacteria. The Schaedler medium marketed by the company Sanofi Diagnostics Pasteur is used as base for anaerobes. The nisin used is obtained from the supplier Sigma (code N5764).

The enrichment supplement comprises hemin (5 mg/l), vitamin K3 (0.5 mg/l) and sodium succinate (2.5 mg/l).

The pH is adjusted to 7.6±0.2.

The strains tested in culture are obtained either from strains deposited at the ATCC or at the Collection de l'Institut Pasteur (CIP), or obtained from hospitals (noted "SDP"). They are the following: *Clostridium perfringens* ATCC 13124, *Clostridium sporogenes* ATCC 11437, *Clostridium sporogenes* ATCC 19404, *Clostridium oedematiens* SDP, *Clostridium sphenoides* SDP, *Bacteroides fragilis* ATCC 25285, *Bacteroides fragilis* SDP 385, *Bacteroides fragilis* SDP 1396, *Bacteroides distasomis* SDP 419, Bacteroides ATCC 130, *Bacteroides vulgatus* ATCC 8482, *Bacteroides vulgatus* CIP 103714, and *Fusobacterium nucleatum* CIP 101130.

Procedure

The Schaedler base and the agar are placed in a solution of one liter of distilled water in proportions as indicated in Table 1. The mixture is heated to boiling temperature and then autoclaved. The other components are then added according to the media described above, A, B and C, using sterile solutions. The preparations obtained are then poured into Petri dishes (round dish of 90 mm) with 5% defibrinated horse blood. The dishes are inoculated from a bacterial suspension using a small rod. The inoculated dishes are then incubated under anaerobic conditions, at 37° C., for 48 hours.

In Table 2 below, the abbreviations of the strains "Bact", "Fuso" and "Clost" mean the strains Bacteroides sp, *Fusobacterium nucleatum* and Clostridium sp respectively.

In Table 2 below, the signs + and − in relation to the different media mean:

−: no growth

+: weak growth (few colonies having a small diameter)

++: good growth (numerous colonies having a large diameter)

+++: very good growth (the colonies can no longer be counted)

TABLE II

| Strain | Gram | No. of Strain | Medium A | | | | Medium B | | | | Medium C | | | |
|---|---|---|---|---|---|---|---|---|---|---|---|---|---|---|
| | | | − | + | ++ | +++ | − | + | ++ | +++ | − | + | ++ | +++ |
| Bact | − | 10 | — | 1 | 4 | 5 | — | 1 | 4 | 5 | — | 1 | 4 | 5 |
| Fuso | − | 1 | — | — | — | 1 | — | — | — | 1 | — | — | — | 1 |
| Clos | + | 5 | 2 | — | — | 3 | 3 | — | 1 | 1 | 4 | 1 | — | — |

It can be observed that the growth of the Gram− bacteria is not modified by the medium used, whereas the growth of the Gram+ bacteria strains is inhibited a great deal more on medium C than on mediums A and B. These results demonstrate that nisin enhances the selectivity of the medium (specificity for the Gram− bacteria) conferred by vancomycin and nalidixic acid, without affecting the sensitivity of the said medium. Indeed, the combination of nisin and vancomycin (medium C of the invention) exhibits an activity greater than the sole addition of the individual effects of the antibiotics (mediums A and B). An unexpected advantageous effect of the antibiotics used according to the invention is therefore observed.

EXAMPLE 2

Selective medium for the isolation of pathogenic Neisseria

1. Tests were carried out to compare the medium according to the invention with a conventional medium and a medium comprising a bacteriocin as sole inhibitor of Gram+ bacteria.

The first medium, designated hereinafter "medium A", contains all the components of the nutrient base enriched with haemoglobin, an enrichment supplement, a selective supplement, whose composition is given below, and vancomycin and teicoplanin as antibiotics active against Gram+ bacteria.

The second medium, designated "medium B", contains all the components of the nutrient base enriched with haemoglobin, an enrichment supplement, the same selective supplement as that of medium A, and a bacteriocin.

The third medium designated "medium C", corresponds to the medium according to the invention and contains all the components present in medium A and medium B.

Procedure

The nutrient agar base is a base for chocolate agar enriched with haemoglobin, marketed by the company Sanofi Diagnostics Pasteur, the composition of which is as follows:

| | |
|---|---|
| Meat peptone | 20 g/l |
| Yeast extract | 3 g/l |
| Meat extract | 3 g/l |
| Starch | 2 g/l |
| Sodium chloride | 5 g/l |
| L-cysteine | 0.01 g/l |
| Agar | 15 g/l |

This base is prepared and autoclaved separately from the other solutions and compounds.

The haemoglobin solution is prepared from haemoglobin powder and is present in the medium at a final concentration of 10 g/l. It is prepared and autoclaved separately from the other solutions and compounds so as to be subsequently sterilely added to the base.

The enrichment supplement is a multivitamin supplement (SPV) marketed by the company Sanofi Diagnostics Pasteur under the trade mark SPV®. This solution is added to the medium at a final volume of 10 ml. The following composition is given for the preparation of one liter of medium according to the invention:

| | |
|---|---|
| Cysteine hydrochloride | 25.9 g |
| Guanine hydrochloride | 0.03 g |
| Thiamine hydrochloride | 0.003 g |
| Co-carboxylase chloride | 0.1 g |
| NAD | 0.25 g |
| Ferric nitrate | 0.02 g |
| Para-aminobenzoic acid | 0.013 g |
| Adenine | 1 g |

-continued

| | |
|---|---|
| L-glutamine | 10 g |
| Vitamin B12 | 0.01 g |
| Glucose | 200 g |

The selective supplement is a mixture composed of an antibiotic active against Gram− bacteria other than Neisseria (colymycin), an antibiotic active against Proteus (trimethoprim) and an agent active against yeasts (amphotericin B).

Each antibiotic is prepared in the form of a sterile solution, either from injectable vials rehydrated with an appropriate solution, or by weighing followed by rehydration and filtration on a 0.22 $\mu$m filter. To prepare 200 ml of each antibiotic solution, each antibiotic is rehydrated in a rehydration solution and sterile water in a quantity sufficient to obtain a final solution of 200 ml. 500 mg of trimethoprim taken up in 500 $\mu$l of lactic acid, 300 mg of amphotericin and $15 \times 10^6$ IU of colymicin are used.

Solutions of vancomycin, teicoplanin and nisin are prepared in the same manner by dissolving 400 mg of teicoplanin, 400 mg of vancomycin and 5 g of nisin respectively, taken up in a few drops of hydrochloric acid in order to obtain 200 ml of solution.

A composition of the media obtained per liter is given in Table III below.

TABLE III

| Constituents | MEDIUM A | MEDIUM B | MEDIUM C |
|---|---|---|---|
| Agar base | 60 g | 60 g | 60 g |
| Enrichment supplement | 10 ml | 10 ml | 10 ml |
| Selective supplement | 6 ml | 6 ml | 6 ml |
| Vancomycin/teicoplanin | 4/4 mg/l | 0 | 4/4 mg/l |
| Nisin | 0 | 50 mg | 50 mg |

The various media prepared are distributed into Petri dishes (diameter 90 mm, volume of 18 ml) according to practices common in bacteriology. These media can be preserved for twelve weeks between 2 and 8° C.

The strains tested in culture are obtained from strains either deposited at the ATCC, or at the Collection de l' Institut Pasteur (CIP), or obtained from hospitals (noted "SDP"). Some Staphylococcus and Enterococcus strains tested have specific profiles of resistance to conventional antibiotics against Gram+ bacteria (these strains are the most representative possible of the cases present in a hospital setting, the minimum inhibitory concentration (MIC) often being high in relation to vancomycin, teicoplanin and other conventional antibiotics). The strains are as follows: *Neisseria meningitidis* SDP 2161, *Neisseria meningitidis* SDP 7612, *Neisseria meningitidis* ATCC 13077, *Neisseria meningitidis* Tiron SDP, *Neisseria meningitidis* ATCC 1913, *Neisseria gonorrhoeae* ATCC 1924, *Neisseria lactamica* SDP 186, *Neisseria gonorrhoeae* Adelaide SDP, *Neisseria gonorrhoeae* Hauch SDP, *Neisseria gonorrhoeae* SDP 345, *Enterococcus faecalis* ATCC 19433, *Enterococcus faecalis* ATCC 29212, Staphylococcus SDP 13/93, Staphylococcus SDP 17/93, Staphylococcus SDP 18/93, Enterococcus SDP 21/93, *Enterococcus faecalis* ATCC 33186.

The bacterial cultures are inoculated according to standard bacteriological methods. Growth and inhibition are observed after 48 hours of incubation under a $CO_2$ atmoshere at 37° C.

TABLE IV

| Strain | No. | Medium A | | | | Medium B | | | | Medium C | | | |
|---|---|---|---|---|---|---|---|---|---|---|---|---|---|
| | | − | + | ++ | +++ | − | + | ++ | +++ | − | + | ++ | +++ |
| Neisseria | 13 | — | — | 3 | 10 | — | — | 3 | 10 | — | — | 3 | 10 |
| Staphylococcus | 3 | 1 | — | 1 | 1 | 1 | — | 1 | 1 | 1 | 2 | — | — |
| Enterococcus | 4 | 2 | 1 | 1 | — | — | — | — | 4 | 3 | 1 | — | — |

In Table IV above, the signs − and + in relation to the various media have the same meaning as that given in Example 1.

It will be noted that the growth of the Neisseria bacteria does not vary according to the medium used. On the other hand, the Gram+ bacteria are scarcely inhibited on mediums A and B, whereas on medium C their growth is greatly inhibited. The results demonstrate that the combination of the antibiotics according to the invention, in medium C, makes it possible to obtain a selectivity greater than that which would be expected by the mere addition of the individual effects of the antibiotics. Indeed, the Staphylococcus and Enterococcus strains which are not completely inhibited by mediums A and B, mostly are on medium C.

We claim:

1. Selective medium for the culture and isolation of Gram− bacteria comprising a nutrient base, at least one antibiotic specifically active against a Gram+ bacteria, and at least one bacteriocin.

2. The medium according to claim 1, characterized in that the antibiotic specifically active against the Gram+ bacteria is selected from the group consisting of vancomycin, teicoplanin, and a combination thereof, and antibiotics of the MLS group, and wherein the bacteriocin is selected from the group consisting of nisin, pediocin A and lacticin.

3. The medium according to claim 1, characterized in that concentration of the antibiotic specifically active against the Gram+ bacteria is between 1 and 10 mg/l and concentration of the bacteriocin is between 10 and 100 mg/l.

4. The medium of claim 1, wherein concentration of the antibiotic specifically active against the Gram+ bacteria is 2.5 mg/l, and concentration of the bacteriocin is between 50 and 60 mg/l.

5. The medium according to claim 1, characterized in that the antibiotic is vancomycin and/or teicoplanin.

6. The medium according to claim 1, characterized in that the bacteriocin is selected from the group consisting of nisin, pediocin A, and lacticin.

7. The medium according to claim 1 further comprising antifungal agents.

8. Selective medium for the culture and isolation of anaerobic Gram− bacteria comprising a nutrient base, at least one antibiotic specifically active against Gram+ bacteria, at least one bacteriocin, and an antibiotic specifically active against Gram− aerobic bacteria.

9. The medium according to claim 8, characterized in that the antibiotic specifically active against Gram− aerobic bacteria is selected from the group consisting of nalidixic acid and aminosides.

10. The medium according to claim 8, wherein the antibiotic specifically active against Gram− aerobic bacteria is kanamycin.

11. The medium according to claim 8, characterized in that the antibiotic specifically active against Gram− aerobic bacteria is present at a concentration of between 5 and 50 mg/l.

12. The medium according to claim 8, wherein concentration of the antibiotic specifically active against Gram[31] aerobic bacteria is 10 mg/l.

13. Selective medium for the culture and isolation of pathogenic Neisseria comprising a nutrient base, at least one antibiotic specifically active against Gram+ bacteria, at least one bacteriocin, and an active agent selected from the group consisting of a mixture of antibiotics active against Gram− bacteria other than Neisseria, a mixture of antibiotics active against Proteus, agents active against yeasts, and a combination, thereof.

14. The medium according to claim 13, characterized in that it contains colymycin, trimethoprim and amphotericin B.

15. The medium according to claim 1, characterized in that the nutrient base is a liquid medium based on agar or a medium with a nutrient agar base.

16. A method of making a selective medium for the culture and isolation of Gram− bacteria comprising combining, in liquid or agar culture media, a bactericidal composition comprising (a) at least one antibiotic specifically active against Gram+ bacteria selected from the group consisting of vancomycin, teicoplanin, and a combination thereof, and antibiotics of the MLS group, and (b) at least one bacteriocin selected from the group consisting of nisin, pediocin A, and lacticin.

17. A method of making a selective medium for the culture and isolation of anaerobic Gram− bacteria comprising combining, in liquid or agar culture media, a bactericidal composition comprising (a) at least one antibiotic specifically active against Gram+ bacteria selected from the group consisting of vancomycin, teicoplanin, and a combination thereof, and antibiotics of the MLS group, (b) at least one bacteriocin selected from the group consisting of nisin, pediocin A, and lacticin, and (c) an antibiotic specifically active against Gram− aerobic bacteria selected from the group consisting of nalidixic acid and aminosides.

18. A method of making a selective medium for the culture and isolation of pathogenic Neisseria comprising combining, in liquid or agar culture media, a bactericidal composition comprising (a) at least one antibiotic specifically active against Gram+ bacteria selected from the group consisting of vancomycin, teicoplanin, and a combination thereof, and antibiotics of the MLS group, and (b) at least one bacteriocin selected from the group consisting of nisin, pediocin A, and lacticin, and (c) colymycin, trimethoprim, and amphotericin B.

19. A method for selectively culturing and isolating Gram− bacteria comprising contacting bacteria with the selective medium of claim 1.

20. A method for selectively culturing and isolating Gram− bacteria comprising contacting bacteria with the selective medium of claim 2.

21. A method for selectively culturing and isolating Gram− bacteria comprising contacting bacteria with the selective medium of claim 3.

22. A method for selectively culturing and isolating Gram− bacteria comprising contacting bacteria with the selective medium of claim 4.

23. A method for selectively culturing and isolating Gram− bacteria comprising contacting bacteria with the selective medium of claim 5.

24. A method for selectively culturing and isolating Gram⁻ bacteria comprising contacting bacteria with the selective medium of claim 6.

25. A method for selectively culturing and isolating Gram⁻ bacteria comprising contacting bacteria with the selective medium of claim 7.

26. A method for selectively culturing and isolating Gram⁻ anaerobic bacteria comprising contacting bacteria with the selective medium of claim 8.

27. A method for selectively culturing and isolating Gram⁻ anaerobic bacteria comprising contacting bacteria with the selective medium of claim 9.

28. A method for selectively culturing and isolating Gram⁻ anaerobic bacteria comprising contacting bacteria with the selective medium of claim 10.

29. A method for selectively culturing and isolating Gram⁻ anaerobic bacteria comprising contacting bacteria with the selective medium of claim 11.

30. A method for selectively culturing and isolating Gram⁻ anaerobic bacteria comprising contacting bacteria with the selective medium of claim 12.

31. A method for selectively culturing and isolating Neisseria bacteria comprising contacting bacteria with the selective medium of claim 13.

32. A method for selectively culturing and isolating Neisseria bacteria comprising contacting bacteria with the selective medium of claim 14.

33. A method for selectively culturing and isolating Gram⁻ bacteria comprising contacting bacteria with the selective medium of claim 15.

\* \* \* \* \*